US00PP35576P2

(12) United States Plant Patent
Lyrene et al.

(10) Patent No.: US PP35,576 P2
(45) Date of Patent: Jan. 16, 2024

(54) BLUEBERRY PLANT NAMED 'FL12-236'

(50) Latin Name: ***Vaccinium corymbosum* L. hybrid**
Varietal Denomination: FL12-236

(71) Applicant: Florida Foundation Seed Producers, Inc., Marianna, FL (US)

(72) Inventors: Paul M. Lyrene, Micanopy, FL (US); James W. Olmstead, Aptos, CA (US); Patricio R. Munoz, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/195,571

(22) Filed: May 10, 2023

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP12,165 P2 10/2001 Lyrene

OTHER PUBLICATIONS https://raintreenursery.com/products/pink-lemonade-blueberry-gal-pot; 6 pages; Aug. 25, 2023.*

* cited by examiner

*Primary Examiner* — Kent L Bell
(74) *Attorney, Agent, or Firm* — Dentons US LLP

(57) ABSTRACT

'FL12-236' is a new and distinct hybrid of southern highbush blueberry (*Vaccinium corymbosum* L.) variety distinguished at least by a low to very low chilling requirement, vigorous and healthy, spreading growth habit, high early yield, good field disease resistance, and large fruit that are very sweet of pink-yellow color and exhibit very small picking scars.

6 Drawing Sheets

Latin name of the genus and species of the plant claimed: *Vaccinium corymbosum* L. hybrid.

Variety denomination: 'FL12-236'.

BACKGROUND OF THE INVENTION

The invention relates to a new and distinct hybrid variety of southern highbush blueberry (*Vaccinium corymbosum* L.) plant 'FL12-236'. 'FL12-236' has a complex pedigree originating from a cross in Gainesville, FL, USA of *V. ashei* (unknown ID) and *V. constablaei* (unknown ID) that developed pink fruit. Pink fruited progeny produced from this cross were pollinated with pollen of *V. corymbosum* (unknown ID), and the fruit of several plants was bulked. Seeds were germinated, and planted near Citra, FL in a high-density nursery in 2010. In 2012, a single clone was selected from the population and assigned the code 'FL12-236'. The plant was clonally propagated and a 15-plant plot was established in Waldo, FL in 2013. These plants were grown for 9 years. 'FL12-236' was first asexually propagated in 2012 by softwood stem cuttings in Gainesville, FL. After 7 years of fruiting in the field, 'FL12-236' was propagated by softwood stem cuttings during the spring of 2020 to establish a large experiment with 1,500 plants that was conducted in January of 2021 in Waldo, FL. All these plots have been observed during flowering and ripening each year since establishment, and no mutations or off-type plants have been observed.

SUMMARY OF THE INVENTION

'FL12-236' differs from its parents and all other known southern highbush blueberry plants. The following are the most distinguishing characteristics of 'FL12-236' when grown under normal horticultural practices in Florida: (1) a low chilling requirement, particularly for the flower buds; (2) a vigorous, spreading growth habit; (3) high and concentrated yield during the month of April; and (4) large, firm, sweet pink-yellow-colored berries that exhibit very small picking scars and strong waxy cover. 'FL12-236' can also be readily and unambiguously distinguished from its parents, at least based on earliness, higher yield, and fruit quality.

Blueberry variety 'Emerald' (U.S. Plant Pat. No. 12,165) is planted throughout the southeastern United States. Plants of 'FL12-236' and 'Emerald' can be readily and unambiguously distinguished at least based upon fruit color, the time at which their fruit is produced, fruit shape, and cluster tightness. Plants of 'FL12-236' display a pink and yellow colored berry, whereas plants of 'Emerald' display standard blue colored fruit. Plants of 'FL12-236' produce their fruit significantly earlier than those of 'Emerald' when no growth regulator is used, and the fruit of 'FL12-236' are rounder and with looser clusters compared to 'Emerald'.

BRIEF DESCRIPTION OF THE DRAWINGS

'FL12-236' is illustrated in the accompanying photographs, which show the plant's flowers, fruit, leaves, and form. Colors shown are as true as can be reasonably reproduced by photographic procedures and may differ from those cited in the detailed description, which accurately describe the colors of 'FL12-236'.

DETAILED BOTANICAL DESCRIPTION

Figure 1:
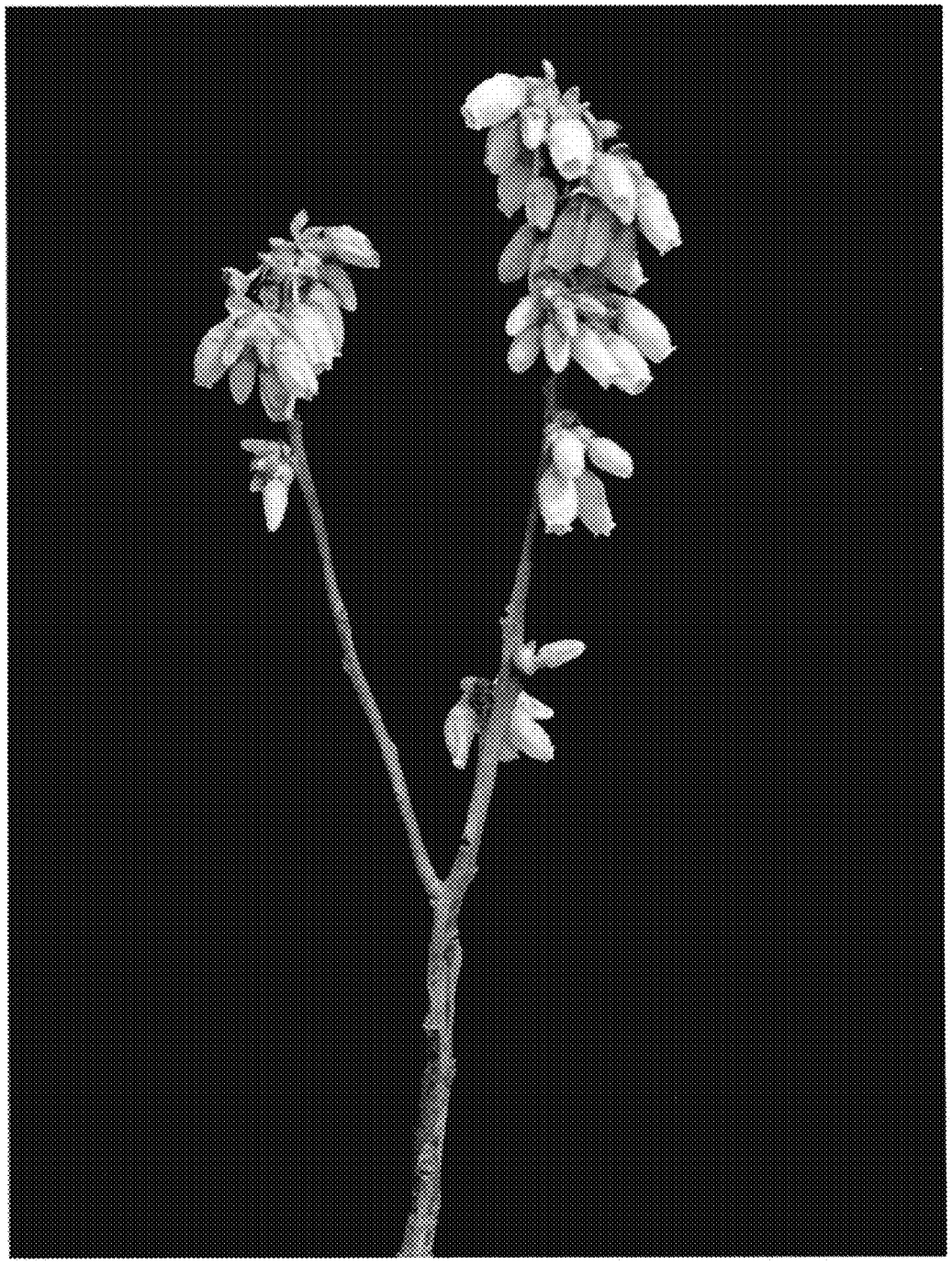
FIG. 1—Shows clusters of opening "FL12-236" flowers.
Figure 2:
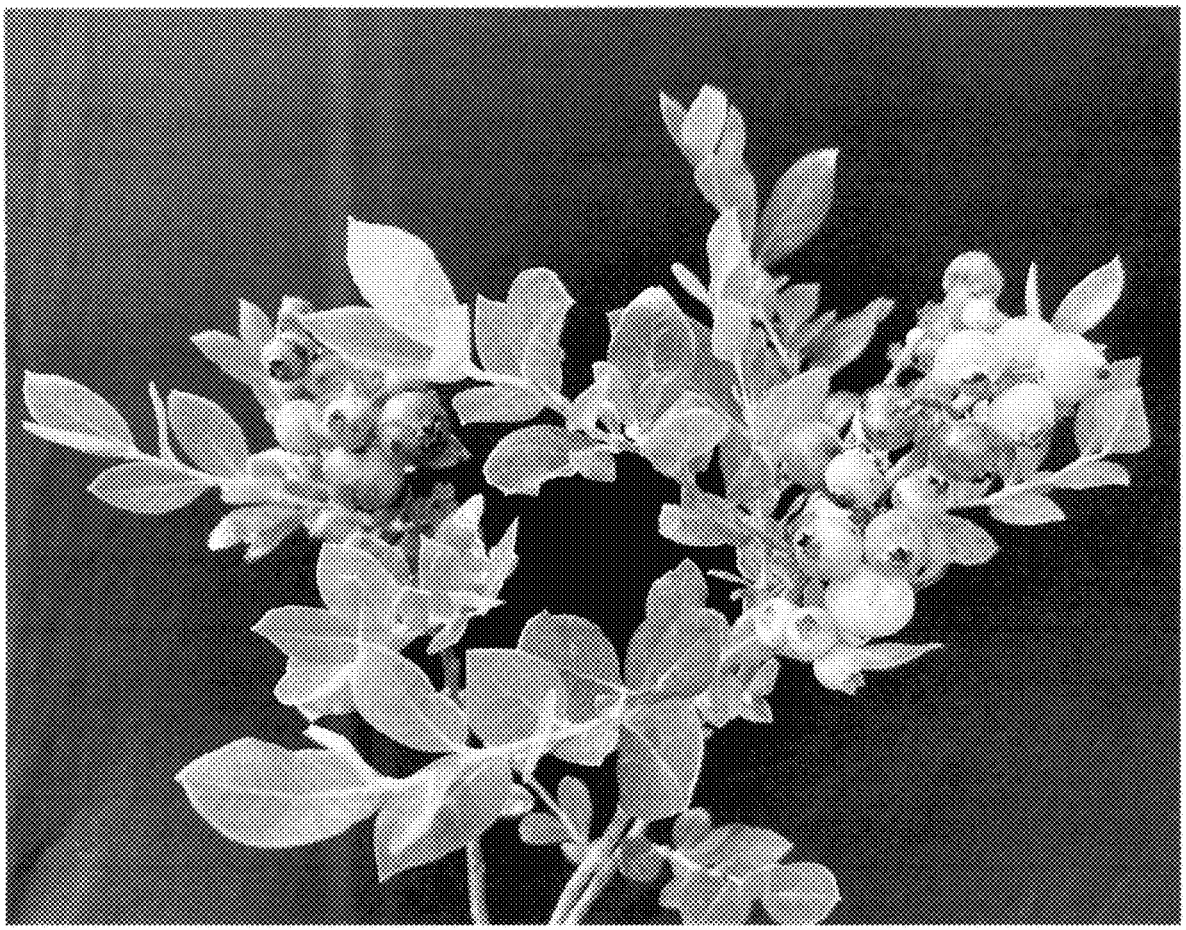
FIG. 2—Shows a cluster of ripe and unripe 'FL12-236' berries.
Figure 3:
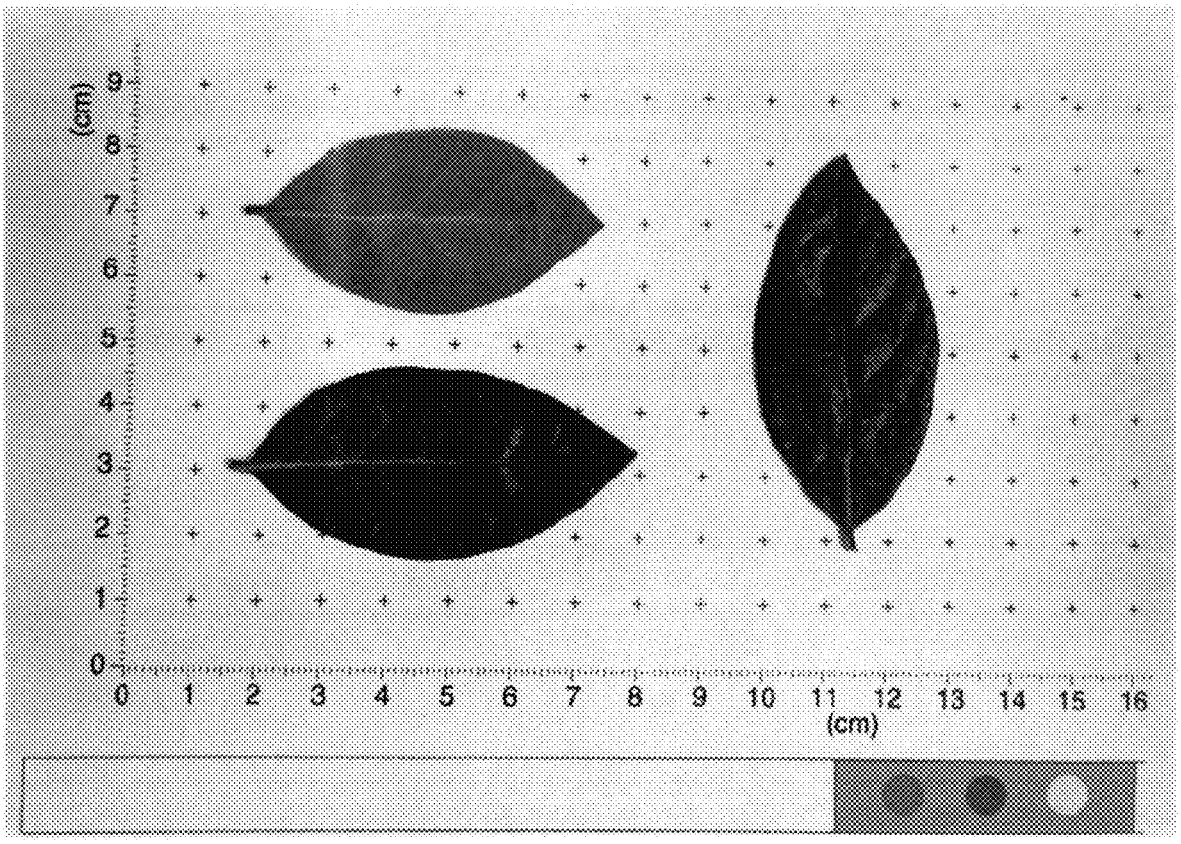
FIG. 3—Shows a close-up of mature 'FL12-236' leaves with a scale bar.
Figure 4:
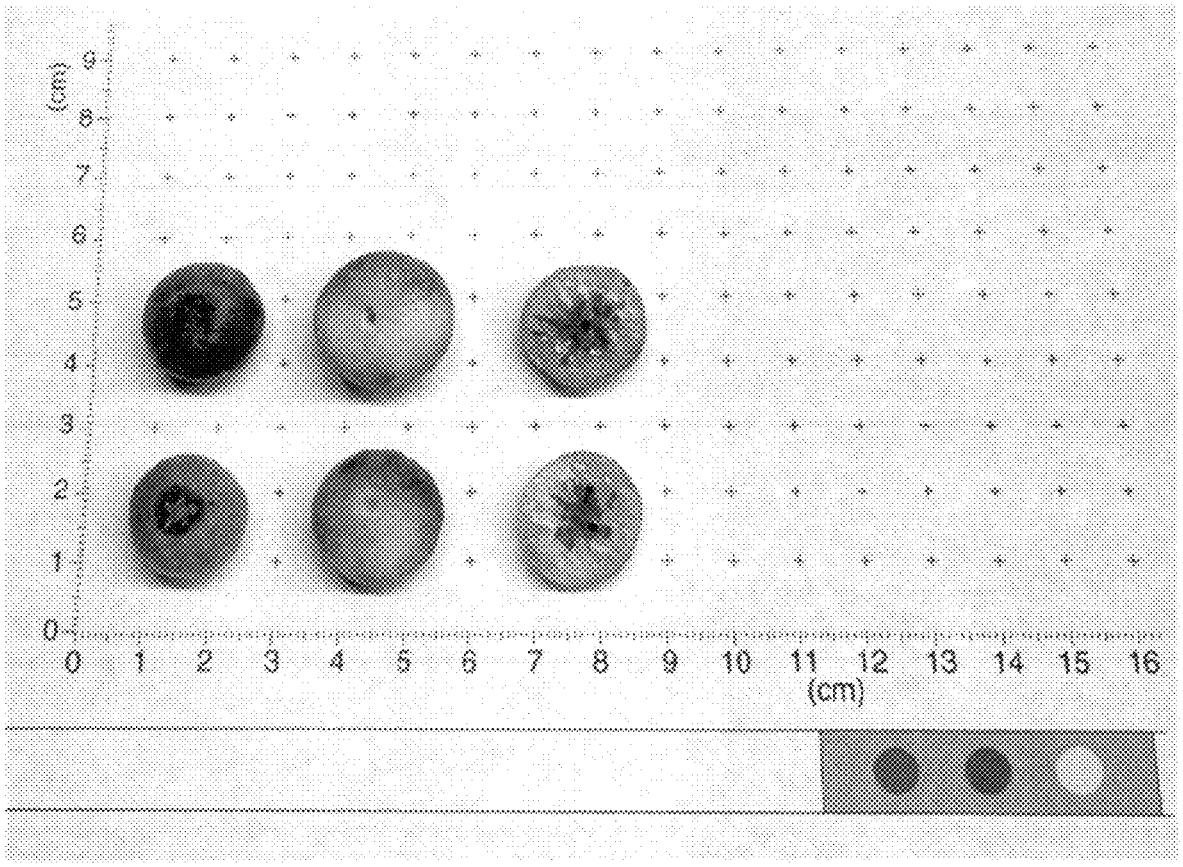
FIG. 4—Shows a close-up of mature 'FL12-236' fruit with a scale bar.
Figure 5:
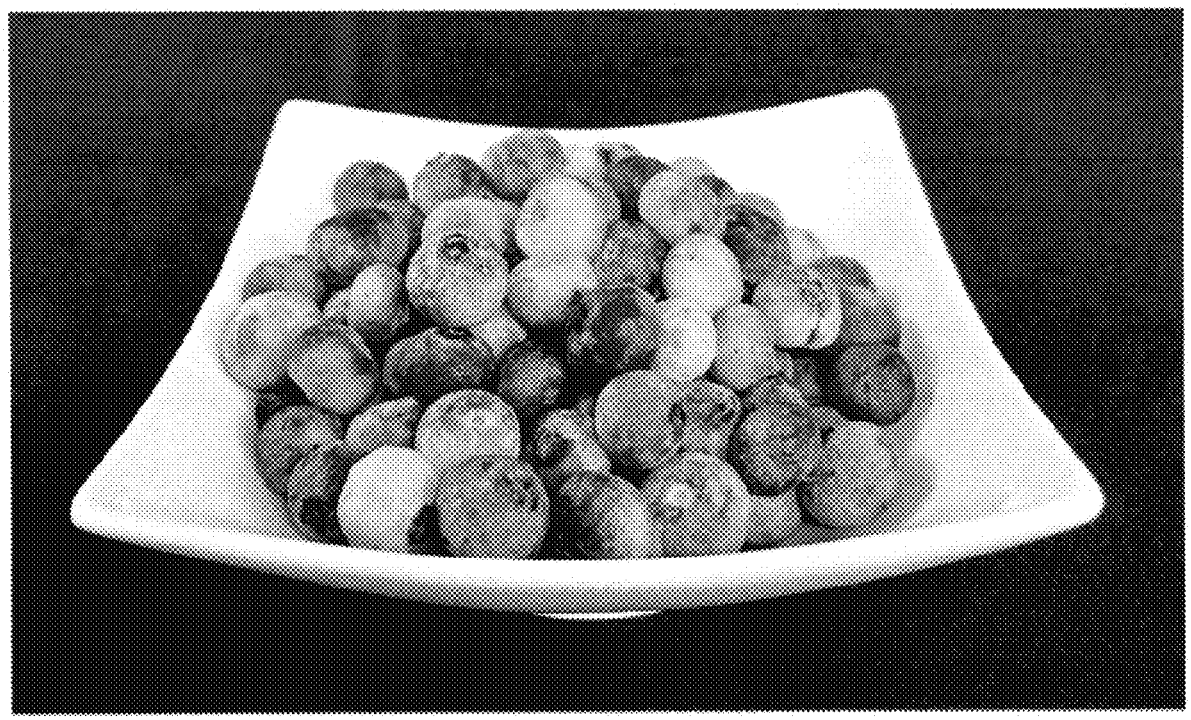
FIG. 5—Shows a close-up of mature harvested 'FL12-236' fruit.
Figure 6:
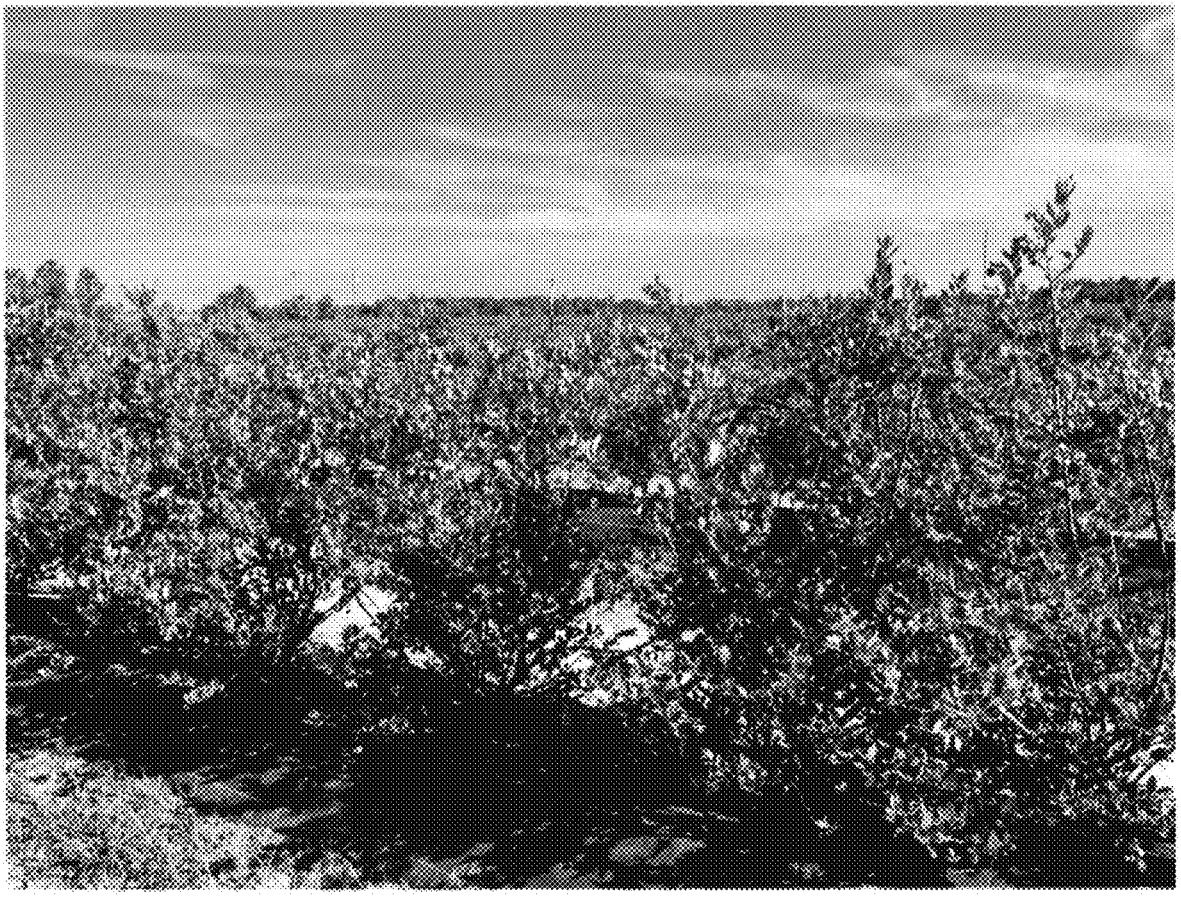
FIG. 6—Shows several two-year-old 'FL12-236' plants on Apr. 27, 2022 with the vigorous, spreading architecture and its potential productivity.

The following detailed description sets forth distinctive characteristics of 'FL12-236'. The data that define these characteristics were collected from asexual reproductions carried out in Florida. The plant history was taken on a plot of plants growing in an experimental trial near Waldo, Florida (W2A Block). The plant was 9 years of age when the data was collected. Certain characteristics may vary with plant age. 'FL12-236' has not been observed under all possible environmental conditions, and the measurements given may vary when grown in different environments. Color descriptions are based on The Royal Horticultural Society (R.H.S.) Colour Chart by The Royal Horticultural Society, London, Fifth Edition, 2007. If any R.H.S. color designations below differ from the accompanying photographs, the R.H.S. color designations are accurate.

Classification:

*Family*.—Ericaceae.

*Botanical*.—*Vaccinium corymbosum*.

*Common name*.—Southern Highbush Blueberry.

*Cultivar name*.—'FL12-236'.

Plant:

*Plant vigor*.—High.

*Growth habit*.—Semi-upright.

*Plant height*.—1.35 m on average for 9-year-old plant.

*Plant spread*.—1.41 m on average for 9-year-old plant.

*Flower bud density* (*number*) *along flowering twigs in January*.—High.

*Twigginess*.—Low to Medium.

*Tendency toward evergreenness*.—It has not been tested for evergreen.

*Productivity*.—In northeast Florida, 'FL12-236' produces 3-4 kg per season from mature plants 3 years old or older when hand harvested.

*Chilling requirement*.—When under chilling 150-200 hours below 7° C.

*Cold hardiness*.—'FL12-236' has been grown in temperate climates with extremely cold winter temperatures. Plants have survived winter freezes of −7° C. with minimal damage.

*Ease of propagation*.—'FL12-236' has only been propagated from softwood stem cuttings, where the rooting percentage is greater than 85% and comparable to other varieties.

Trunk and branches:

*Suckering tendency*.—Low.

*Surface texture* (*of strong, 12-month-old shoots*).—Moderately Smooth with small micro-size bumps along the shoot.

*Surface texture* (*of 3-year-old and older wood*).—Moderately rough texture with peeling bark along the wood.

*Color of new twigs observed in the field*.—Fan 3 Yellow-green group 144 strong yellow-green C.

*Color of 3-year-old, rough-textured canes*.—Fan 4 Brown Group N200 Light gray D with Fan 3 Yellow Green Group 144 strong yellow-green D on area exposed by the peeling bark.

*Internode length* (*strong, upright shoots measured in June*).—Mean of 14.54 mm.

Leaves:

*Leaf arrangement*.—Alternate, Fibonacci Spiral.

*Length* (*including petiole, from tip of petiole to end of blade*).—Mean of 5.24 cm.

*Width* (*at widest point*).—Mean of 2.69 cm.

*Petiole length*.—Mean of 3.30 mm.

*Petiole diameter*.—Mean of 1.59 mm.

*Leaf shape*.—Elliptic slightly falcate towards the leaf apex with the leaf apex having a small point.

*Leaf base shape*.—Obovate tapering from center to leaf base.

*Leaf venation pattern*.—Reticulate.

*Margin*.—Entire.

*Color*.—Upper surface: Fan 3 green group 137 moderate olive green A. Lower surface: Fan 3 green group 138 moderate yellow green B. Leaf Vein Color: Fan 3 yellow-green group 151 strong Greenish Yellow A. Leaf petiole color: Fan 3 yellow green group 151 strong greenish yellow A with highlights on upper side and back of Fan 2 Red Purple Group 61 Deep Purplish Red A.

*Pubescence*.—Upper surface of leaves: Absent. Lower surface of leaves: Absent. Margins: Absent.

*Timing of vegetative bud burst* (*early, medium, late*).—Medium.

*Relative time of leafing versus flowering*.—When not treated with hydrogen cyanamide in mid-winter, leafing occurs after flowering.

Flowers:

*Arrangement*.—Flowers are arranged in tight clusters of flowers spiraling along branches without leaves.

*Fragrance*.—Very slight floral fragrance.

*Shape*.—Urceolate, more round with slight oval, moderate radiations.

*Flowering period*.—Mean date of 70% anthesis at Windsor, Florida, is week 8 of the year.

*Cluster*.—Tight cluster.

*Number of flowers per cluster*.—Mean of 7.12.

*Pedicel*.—Length at time of anthesis: Mean of 5.14 mm. Color at time of anthesis: Fan 3 yellow-green group N144 strong-yellow green D with hints of Fan 2 red-purple group 67 strong purplish red A on sun-exposed side.

*Peduncle*.—Length at time of anthesis: Variable, mean of 8.62 mm. Color at time of anthesis: Fan 3 yellow-green group N144 strong yellow-green D with hints of Fan 2 red purple group 67 strong Purplish red A on the sun exposed side.

*Calyx*.—Surface texture: Very Smooth with slight wax. Diameter: Mean of 4.67 mm. Color (outer surface, visible at the time of anthesis without removing the corolla tube): Fan 3 Yellow-green group 144 Strong Yellow green A with Fan 3 yellow-green group 144 Strong Yellow Green C on tips of calyx lobes.

*Corolla*.—Diameter: mean of 5.53 mm. Length (from pedicel attachment point to corolla tip excluding the pedicel): Mean of 11.47 mm. Aperture diameter: Mean of 3.13 mm. Texture: Smooth with slight radiations. Color: Fan 4 white group 155 Pale Yellow Green A. Anthocyanin coloration in tube: Slight Presence on corolla base.

Reproductive organs:

*Style*.—Length (top of ovary to stigma tip): Mean of 9.84 mm. Color: Fan 3 yellow-green group 145 Light Yellow green C.

*Location of tip of stigma relative to lip of the corolla*.—Stigma tip is approximately even to 86 mm below the corolla lip.

*Anthers*.—Color: Fan 4 greyed-orange group 167 moderate orange B. Pollen: High. Pollen germination: Typically, greater 90%. Color: Fan 4 white group 155 Pale Yellow Green A. Filament length: 3.93 mm. Filament width: 1.06 mm.

*Self-fruitfulness*.—Low to medium. Planting in the field configurations that promote cross-fertilization with other southern highbush varieties is recommended for all southern highbush blueberry plants grown in Florida.

Fruit:

*Mean date of* 50% *harvest in Waldo, Florida*.—Week 15-16 of the year.

*Diameter of calyx aperture on mature berry*.—Mean of 4.96 mm.

*Size and shape of calyx lobes on mature berry*.—Very small, very erect to incurving at the tip of the lobe, with a moderate shallow calyx basin.

*Pedicel length on ripe berry*.—Mean of 6.14 mm.

*Detachment force for ripe berries* (*easy, medium, hard*).—Easy.

*Fruit cluster density* (*sparse, medium, dense*).—Medium.

*Number of berries per cluster*.—Mean of 4.

*Fruiting type*.—On current season's shoots.

Berry:

*Cluster* (*tight, medium, loose*).—Medium.

*Weight* (*on well-pruned plants*).—Mean of 2.52 g per berry.

*Weight of* 25 *berries*.—63.11 g.

*Height*.—Mean of 13.85 mm.

*Width*.—Mean of 15.65 mm.

*Shape*.—Round & slight oblate.

*Surface color of mature berries ripe on the plant*.—Fan 1 Green Yellow Group 1 Pale Greenish Yellow D with blush accents ranging from Fan4 Greyed-Purple group 185 Moderate Red B to Moderate Purplish Red C to Deep Pink D.

*Intensity of fruit bloom*.—High.

*Surface color of ripe berry after polishing*.—Fan 3 Yellow-Green Group 150 Brilliant Yellow Green C with Blush accent color ranging from Fan 2 Red-Purple Group 61 Deep-Purplish Red A to Vivid Purplish Red C.

*Immature berry color, with bloom*.—Fan 3 Yellow green Group 145 Light yellow green C.

*Immature berry color, without bloom*.—Fan 3 Yellow Green Group 144 Light Yellow Green D.

*Flesh color*.—Fan 4 white group NN155 Bluish White A with hints of Fan 3 Yellow-Green Group 150 Brilliant Yellow Green C.

*Surface wax*.—Medium High with moderate persistence.

*Pedicel scar*.—Very Small scar and dry. Average 1.04 mm.

*Firmness*.—Very firm. Mean 297.15 g/mm.

*Flavor*.—When Yellow with pink Blush: Pleasant balance of sweet and tanginess. When Color of fruit is predominantly pink the sweetness is increased with hints of a tangy peach flavor.

*Intensity of fruit sweetness*.—High.

*Texture*.—Very Good texture (firm, non-mealy flesh) crispy. High juiciness.

*Fruit storage quality*.—Fruit is unusually firm and can be stored without shriveling, mold or loss of firmness for 3-4 weeks at 4° C.

Seeds:

*Color of dried seeds*.—Fan 4 Greyed Orange group N167 Brownish Orange A.

*Weight of* 25 *well-developed dried seeds*.—Mean of 17 mg.

*Length of well-developed dried seeds*.—Mean of 2.22 mm.

*Width of well-developed dried seeds*.—Mean of 1.26 mm.

Use: Produces southern highbush blueberries suitable for hand harvest for the fresh fruit markets.

Resistance to diseases, insects, and mites: Has grown vigorously and shows good bush survival in the field, with almost no plants dying soon after planting. Reaction to the various fungal species that cause summer leaf spots (including rust) is lower than those of other southern highbush varieties. Fungicide applications may be needed after harvest to reduce foliar diseases and retain leaves into the fall for maximum flower bud set. Appears to be more tolerant than other southern highbush varieties to spider mites. Susceptibility to typical blueberry insect and mite pathogens such as spotted wing drosophila (*Drosophila suzukii*), blueberry gall midge (*Dasineura oxycoccana*), blueberry chilly thrips (*Scirtothips dorsalis*), blueberry flower thrips (*Frankliniella* spp), and blueberry bud mite (*Acalitus vaccini*) appear like other southern highbush cultivars.

What is claimed is:

1. A new and distinct variety of southern highbush blueberry plant named 'FL12-236', as illustrated and described herein.

* * * * *